US006759545B2

(12) United States Patent
Yanagisawa et al.

(10) Patent No.: US 6,759,545 B2
(45) Date of Patent: Jul. 6, 2004

(54) ORGANOSILICON COMPOUNDS AND PREPARATION PROCESSES

(75) Inventors: Hideyoshi Yanagisawa, Gunma-ken (JP); Masaaki Yamaya, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/114,990

(22) Filed: Apr. 4, 2002

(65) Prior Publication Data

US 2002/0147358 A1 Oct. 10, 2002

(30) Foreign Application Priority Data

Apr. 6, 2001 (JP) ........................................ 2001-107982

(51) Int. Cl.$^7$ ................................................. C07F 7/02
(52) U.S. Cl. ..................................................... 556/427
(58) Field of Search ............................ 556/427; 544/63, 544/69

(56) References Cited

U.S. PATENT DOCUMENTS

| | | | |
|---|---|---|---|
| 4,709,065 A | | 11/1987 | Yoshioka et al. |
| 5,583,245 A | * | 12/1996 | Parker et al. ................ 556/427 |
| 5,663,226 A | | 9/1997 | Scholl et al. |
| 5,780,531 A | | 7/1998 | Scholl |
| 5,827,912 A | | 10/1998 | Scholl |
| 6,194,594 B1 | * | 2/2001 | Gorl et al. ................... 556/427 |
| 6,300,397 B1 | * | 10/2001 | Sandstrom et al. .......... 524/262 |
| 6,423,859 B1 | * | 7/2002 | Alig et al. ................... 556/427 |
| 6,534,668 B2 | * | 3/2003 | Backer et al. ............... 556/427 |
| 2003/0027966 A1 | * | 2/2003 | Yanagisawa ................. 528/10 |
| 2003/0176719 A1 | * | 9/2003 | Yanagisawa et al. ........ 556/427 |
| 2003/0236424 A1 | * | 12/2003 | Yanagisawa et al. ........ 556/427 |

FOREIGN PATENT DOCUMENTS

| | | |
|---|---|---|
| DE | 44 24 582 A1 | 1/1996 |
| EP | 0 670 347 A1 | 9/1995 |
| EP | 0 748 839 A1 | 12/1996 |
| EP | 0 753 549 A2 | 1/1997 |
| SE | 465 267 B | 8/1991 |
| WO | WO 02/20534 A1 | 3/2002 |

OTHER PUBLICATIONS

CA:137:263179 abs of EP 1247812 Oct. 2002.*
CA:133:266973 abs of JP2000264891 Sep. 2000.*
CA:114:143510 abs of Tetrahedron Letters by Stjernloef et al 31(40) pp 5773–5774 1990.*
CA:120:177984 abs of Chemistry Letters by Ichinose et al (11) pp 1961–1964 1993.*
CA:123:97953 abs of JP07084371 Mar. 1995.*
CA:114:143510 abs of Tetrahedron Letters by Stjernloef et al 31(40) pp 5773–5774 1990.*
Stjernlöf et al., Tetrahedron Letters, vol. 31, No. 40 (1990) pp. 5773–5774.

* cited by examiner

*Primary Examiner*—Jean F. Vollano
(74) *Attorney, Agent, or Firm*—Birch, Stewart, Kolasch & Birch, LLP

(57) ABSTRACT

Organosilicon compounds having an organooxysilyl group at one end and a monovalent hydrocarbon group at the other end of the molecule and containing a polysulfide group and organosilicon compounds having organooxysilyl groups at both ends of the molecule and containing a divalent hydrocarbon group flanked with polysulfide groups at a center thereof are useful as a compounding additive to inorganic-organic composite materials and a surface treating agent for fillers, Processes capable of effective preparation of these organosilicon compounds are also provided.

13 Claims, No Drawings

ORGANOSILICON COMPOUNDS AND PREPARATION PROCESSES

This invention relates to novel organosilicon compounds and processes for preparing the same. More particularly, it relates to novel organosilicon compounds having an organooxysilyl group at one end of a molecule and a monovalent hydrocarbon group at the other end thereof and containing a polysulfide group as well as novel organosilicon compounds having organooxysilyl groups at both ends of a molecule and containing a divalent hydrocarbon group flanked with polysulfide groups at a center thereof.

BACKGROUND OF THE INVENTION

Compounds containing alkoxysilyl and polysulfide groups within the molecule are known in the art. These compounds are used as an interfacial binder between inorganic materials such as silica, aluminum hydroxide and talc and organic materials such as thermosetting resins, thermoplastic resins and rubber, an adhesion modifier for organic resins and rubber, a primer composition or the like.

While sulfide group-containing organosilicon compounds are applied to composite materials composed of resins or rubber and inorganic materials as mentioned above, compositions obtained by adding known sulfide group-containing organosilicon compounds to resins or rubber and mixing them with inorganic materials suffer from insufficient abrasion resistance.

SUMMARY OF THE INVENTION

An object of the invention is to provide novel organosilicon compounds having overcome these disadvantages and drawbacks, and processes for preparing the same.

In one aspect, the invention provides an organosilicon compound having the following general formula (1):

$$(R^1O)_{(3-p)}(R^2)_p Si\text{—}R^3\text{—}S_m\text{—}R^4\text{—}A \tag{1}$$

wherein $R^1$ and $R^2$ each are a monovalent hydrocarbon group having 1 to 4 carbon atoms, $R^3$ and $R^4$ each are a divalent hydrocarbon group having 1 to 10 carbon atoms, A is hydrogen or the moiety: —$S_m$—$R^3$—$Si(OR^1)_{(3-p)}(R^2)_p$, m is 2 to 10, and p is equal to 0, 1 or 2.

In one embodiment of the process according to the invention, the organosilicon compound of formula (1) is prepared by the step of reacting a haloalkyl group-containing organosilicon compound of the following general formula (2):

$$(R^1O)_{(3-p)}(R^2)_p Si\text{—}R^3\text{—}X \tag{2}$$

wherein $R^1$ and $R^2$ each are a monovalent hydrocarbon group having 1 to 4 carbon atoms, $R^3$ is a divalent hydrocarbon group having 1 to 10 carbon atoms, X is halogen, and p is equal to 0, 1 or 2, and a halogen-containing compound of the following general formula (3):

$$X\text{—}R^4\text{—}Y \tag{3}$$

wherein $R^4$ is a divalent hydrocarbon group having 1 to 10 carbon atoms, X is halogen, and Y is hydrogen or halogen, with an anhydrous sodium sulfide or polysulfide having the following general formula (4):

$$Na_2S_q \tag{4}$$

wherein q is 1 to 4, and optionally, sulfur.

In another embodiment of the process according to the invention, the organosilicon compound of formula (1) is prepared by the step of reacting a mercaptoalkyl group-containing organosilicon compound of the following general formula (5):

$$(R^1O)_{(3-p)}(R^2)_p Si\text{—}R^3\text{—}SH \tag{5}$$

wherein $R^1$ and $R^2$ each are a monovalent hydrocarbon group having 1 to 4 carbon atoms, $R^3$ is a divalent hydrocarbon group having 1 to 10 carbon atoms, and p is equal to 0, 1 or 2, with a sulfenamide group-containing compound of the following general formula (6):

$$(R^5)(R^6)N\text{—}S\text{—}R^4\text{—}B \tag{6}$$

wherein $R^4$ is a divalent hydrocarbon group having 1 to 10 carbon atoms, $R^5$ and $R^6$ each are independently hydrogen or a monovalent hydrocarbon group having 1 to 6 carbon atoms, with the proviso that $R^5$ and $R^6$ are not hydrogen at the same time, or $R^5$ and $R^6$, taken together, form a divalent hydrocarbon group having 4 to 10 carbon atoms which may contain a nitrogen, oxygen or sulfur atom, and B is hydrogen or the moiety: —S—N($R^5$)($R^6$).

In a further embodiment of the process according to the invention, the organosilicon compound of formula (1) is prepared by the step of reacting a sulfenamide group-containing organosilicon compound of the following general formula (7):

$$(R^1O)_{(3-p)}(R^2)_p Si\text{—}R^3\text{—}S\text{—}N(R^5)(R^6) \tag{7}$$

wherein $R^1$ and $R^2$ each are a monovalent hydrocarbon group having 1 to 4 carbon atoms, $R^3$ is a divalent hydrocarbon group having 1 to 10 carbon atoms, $R^5$ and $R^6$ each are independently hydrogen or a monovalent hydrocarbon group having 1 to 6 carbon atoms, with the proviso that $R^5$ and $R^6$ are not hydrogen at the same time, or $R^5$ and $R^6$, taken together, form a divalent hydrocarbon group having 4 to 10 carbon atoms which may contain a nitrogen, oxygen or sulfur atom, and p is equal to 0, 1 or 2, with a mercapto group-containing compound of the following general formula (8):

$$HS\text{—}R^4\text{—}Z \tag{8}$$

wherein $R^4$ is a divalent hydrocarbon group having 1 to 10 carbon atoms, and Z is hydrogen or SH.

DESCRIPTION OF THE PREFERRED EMBODIMENTS

The organosilicon compounds of the invention are of the general formula (1).

$$(R^1O)_{(3-p)}(R^2)_p Si\text{—}R^3\text{—}S\text{—}R^4\text{—}A \tag{1}$$

Herein $R^1$ and $R^2$ each are a monovalent hydrocarbon group having 1 to 4 carbon atoms, for example, alkyl and alkenyl groups such as methyl, ethyl, n-propyl, i-propyl, n-butyl, i-butyl, t-butyl, allyl and methallyl. $R^3$ and $R^4$ each are a divalent hydrocarbon group having 1 to 10 carbon atoms, for example, alkylene, arylene and alkenylene groups such as methylene, ethylene, propylene, n-butylene, i-butylene, hexylene, decylene, phenylene, and methylphenylethylene, and mixtures thereof. A is hydrogen or the moiety: —$S_m$—$R^3$—$Si(OR^1)_{(3-p)}(R^2)_p$, m is 2 to 10, and p is equal to 0, 1 or 2.

Typical, non-limiting examples of the compound of formula (1) are given below.

(CH$_3$O)$_3$Si—(CH$_2$)$_3$—S$_4$—CH$_2$CH$_2$CH$_2$CH$_2$CH$_2$CH$_3$ (CH$_3$CH$_2$O)$_3$Si—(CH$_2$)$_3$—S$_2$—CH$_2$CH$_2$CH$_2$CH$_2$CH$_2$CH$_3$ (CH$_3$O)$_3$Si—(CH$_2$)$_3$—S$_4$—(CH$_2$)$_9$CH$_3$ (CH$_3$O)$_3$Si—(CH$_2$)$_3$—S$_2$—CH$_2$CH=CH$_2$ (CH$_3$CH$_2$O)$_3$Si—(CH$_2$)$_3$—S$_3$—CH$_2$CH=CH$_2$ (CH$_3$CH$_2$O)$_3$Si—(CH$_2$)$_3$—S$_2$—CH$_2$CH$_2$CH$_2$CH$_2$CH$_2$CH$_2$—S$_2$—(CH$_2$)$_3$—Si(OCH$_2$CH$_3$)$_3$ (CH$_3$CH$_2$O)$_3$Si—(CH$_2$)$_3$—S$_4$—CH$_2$CH$_2$CH$_2$CH$_2$CH$_2$CH$_2$—S$_4$—(CH$_2$)$_3$—Si(OCH$_2$CH$_3$)$_3$ (CH$_3$CH$_2$O)$_3$Si—(CH$_2$)$_3$—S$_2$—(CH$_2$)$_{10}$—S$_2$—(CH$_2$)$_3$—Si(OCH$_2$CH$_3$)$_3$

In the aforementioned compound, sulfur is merely represented by an average value because it has a distribution due to disproportionation reaction or the like. In formula (1), m has an average value of 1 to 10, preferably 2 to 4, and more preferably 2 to 3.

In one embodiment, the organosilicon compound of formula (1) is prepared by the step of reacting a haloalkyl group-containing organosilicon compound of the following general formula (2):

$$(R^1O)_{(3-p)}(R^2)_p Si-R^3-X \quad (2)$$

and a halogen-containing compound of the following general formula (3):

$$X-R^4-Y \quad (3)$$

with an anhydrous sodium sulfide or anhydrous sodium polysulfide having the following general formula (4):

$$Na_2S_q \quad (4)$$

and optionally, sulfur.

In another embodiment, the organosilicon compound of formula (1) is prepared by the step of reacting a mercaptoalkyl group-containing organosilicon compound of the following general formula (5):

$$(R^1O)_{(3-p)}(R^2)_p Si-R^3-SH \quad (5)$$

with a sulfenamide group-containing compound of the following general formula (6):

$$(R^5)(R^6)N-S-R^4-B \quad (6).$$

In a further embodiment, the organosilicon compound of formula (1) is prepared by the step of reacting a sulfenamide group-containing organosilicon compound of the following general formula (7):

$$(R^1O)_{(3-p)}(R^2)_p Si-R^3-S-N(R^5)(R^6) \quad (7)$$

with a mercapto group-containing compound of the following general formula (8):

$$HS-R^4-Z \quad (8).$$

In the above formulae, R$^1$, R$^2$, R$^3$, R$^4$ and p are as defined above.

R$^5$ and R$^6$ are independently selected from hydrogen and monovalent hydrocarbon groups having 1 to 6 carbon atoms, for example, alkyl groups such as methyl, ethyl, n-propyl and i-propyl, alkenyl groups such as vinyl and allyl, and phenyl. R$^5$ and R$^6$ may be the same or different, with the proviso that R$^5$ and R$^6$ are not hydrogen at the same time. Alternatively, R$^5$ and R$^6$ may form a ring with the nitrogen atom and in this event, they form a divalent hydrocarbon group having 4 to 10 carbon atoms which may contain a nitrogen, oxygen or sulfur atom, for example, alkylene, arylene, alkenylene or mixtures thereof.

X is a halogen atom such as chlorine; Y is hydrogen or a halogen atom; B is hydrogen or the moiety: —S—N(R$^5$)(R$^6$); Z is hydrogen or a SH group; and q is a number of 1 to 4.

Typical, non-limiting examples of the compound of formula (2) are given below.

(CH$_3$O)$_3$Si—(CH$_2$)$_3$—Cl (CH$_3$CH$_2$O)$_3$Si—(CH$_2$)$_3$—Cl (CH$_3$O)$_3$Si—(CH$_2$)$_4$—Cl (CH$_3$O)$_3$Si—(CH$_2$)$_6$—Br (CH$_3$O)$_3$Si—(CH$_2$)$_{10}$—Br (CH$_3$O)$_3$Si—CH$_2$CH(CH$_3$)CH$_2$—Cl (CH$_3$CH$_2$O)$_3$Si—CH$_2$CH(CH$_3$)CH$_2$—Cl

Typical, non-limiting examples of the compound of formula (3) are given below.

Cl—CH$_2$CH$_2$CH$_2$CH$_3$

Cl—(CH$_2$)$_5$CH$_3$

Cl—(CH$_2$)$_9$CH$_3$

Cl—CH$_2$CH=CH$_2$

Cl—(CH$_2$)$_6$—Cl

Br—(CH$_2$)$_5$CH$_3$

Cl—CH$_2$C(CH$_3$)=CH$_2$

Illustrative examples of the compound of formula (4) are Na$_2$S, Na$_2$S$_2$, Na$_2$S$_3$ and Na$_2$S$_4$.

Anhydrous sodium sulfide Na$_2$S falling in the class of compound (4) may be prepared by dehydrating hydrous sodium sulfide, or reacting sodium sulfide with sodium alcoholate in an anhydrous state, or reacting metallic sodium or potassium with sulfur in an anhydrous state. Anhydrous sodium polysulfide used herein may be one obtained by dehydrating hydrous sodium polysulfide, or reacting the above anhydrous sodium sulfide with sulfur in an anhydrous state, or reacting metallic sodium or potassium with sulfur in an anhydrous state.

Typical, non-limiting examples of the compound of formula (5) are given below.

(CH$_3$O)$_3$Si—(CH$_2$)$_3$—SH (CH$_3$CH$_2$O)$_3$Si—(CH$_2$)$_3$—SH (CH$_3$O)$_3$Si—(CH$_2$)$_4$—SH (CH$_3$O)$_3$Si—(CH$_2$)$_6$—SH (CH$_3$O)$_3$Si—(CH$_2$)$_{10}$—SH (CH$_3$O)$_3$Si—CH$_2$CH(CH$_3$)CH$_2$—SH (CH$_3$CH$_2$O)$_3$Si—CH$_2$CH(CH$_3$)CH$_2$—SH

Typical, non-limiting examples of the compound of formula (6) are given below.

(CH$_3$)$_3$C—NH—S—CH$_2$CH$_2$CH$_2$CH$_3$ (CH$_3$)$_3$C—NH—S—(CH$_2$)$_5$CH$_3$ (CH$_3$)$_3$C—NH—S—(CH$_2$)$_9$CH$_3$ (CH$_3$)$_3$C—NH—S—CH$_2$CH=CH$_2$ (CH$_3$)$_3$C—NH—S—(CH$_2$)$_6$—S—NHC(CH$_3$)$_3$

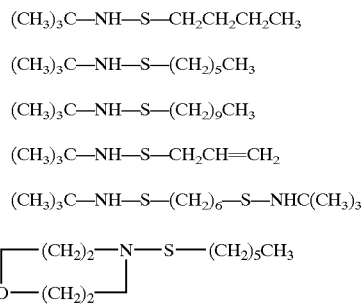

Typical, non-limiting examples of the compound of formula (7) are given below.

(CH$_3$O)$_3$Si—(CH$_2$)$_3$—S—NH—C(CH$_3$)$_3$ (CH$_3$CH$_2$O)$_3$Si—(CH$_2$)$_3$—S—NH—C(CH$_3$)$_3$ (CH$_3$O)$_3$Si—(CH$_2$)$_4$—S—NH—C(CH$_3$)$_3$ (CH$_3$O)$_3$Si—(CH$_2$)$_6$—S—NH—C(CH$_3$)$_3$ (CH$_3$O)$_3$Si—(CH$_2$)$_{10}$—S—NH—C(CH$_3$)$_3$ (CH$_3$O)$_3$Si—CH$_2$CH(CH$_3$)CH$_2$—S—NH—C(CH$_3$)$_3$ (CH$_3$CH$_2$O)$_3$Si—CH$_2$CH(CH$_3$)CH$_2$—S—NH—C(CH$_3$)$_3$

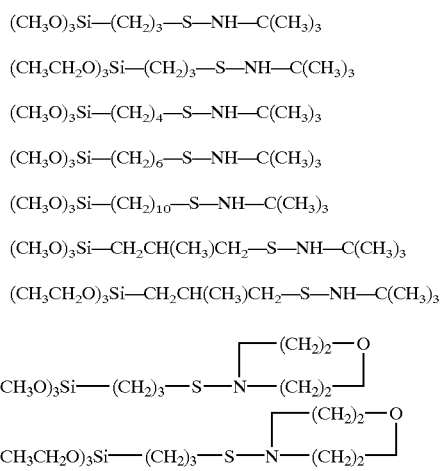

Typical, non-limiting examples of the compound of formula (8) are given below.

HS—CH$_2$CH$_2$CH$_2$CH$_3$

HS—(CH$_2$)$_5$CH$_3$

HS—(CH$_2$)$_9$CH$_3$

HS—CH$_2$CH=CH$_2$

HS—(CH$_2$)$_6$—SH

HS—CH$_2$C(CH$_3$)=CH$_2$

When the organosilicon compound is prepared by reacting a haloalkyl group-containing organosilicon compound of the formula (2): (R$^1$O)$_{(3-p)}$(R$^2$)$_p$Si—R—X and a halogen-containing compound of the formula (3): X—R$^4$—Y with an anhydrous sodium sulfide or polysulfide of the formula (4): Na$_2$S$_q$ and optionally, sulfur, use of a solvent is arbitrary. Examples of the solvent, if used, include hydrocarbons such as pentane, hexane, heptane, octane, benzene, toluene and xylene, alcohols such as methanol and ethanol, ethers such as dibutyl ether, tetrahydrofuran and dioxane, ketones such as methyl ethyl ketone and methyl isobutyl ketone, esters such as ethyl acetate, and amides such as dimethylformamide. Inter alia, alcohols such as methanol and ethanol are preferred. The reaction temperature is generally in the range of about 0° C. to 150° C., preferably about 50° C. to 100° C. The reaction time may continue until the sodium sulfide or sodium polysulfide is consumed, and generally ranges from about 30 minutes to about 20 hours. The way of reaction is arbitrary and, for example, involves charging the compound of formula (4) and optionally, sulfur and solvent, and adding dropwise a mixture of the compounds of formulae (2) and (3) or adding dropwise the compound of formula (2) and then adding dropwise the compound of formula (3). An alternative way involves charging the compounds of formulae (2) and (3) and optionally, sulfur and solvent, and gradually admitting the compound of formula (4).

Preferably, the molar ratio of the respective components during reaction is set as follows. The molar ratio of the haloalkyl group-containing organosilicon compound of formula (2) to the halogen-containing compound of formula (3) may be 1:0.9–1.1. The molar ratio of halogens in the haloalkyl group-containing organosilicon compound of formula (2) and the halogen-containing compound of formula (3) to sodium in the anhydrous sodium sulfide or polysulfide of formula (4) may be 1:0.9–1.1. The amount of sulfur added is arbitrary although at least (m-q) mol of sulfur may be added.

When the organosilicon compound is prepared by reacting a mercaptoalkyl group-containing organosilicon compound of the formula (5): (R$^1$O)$_{(3-p)}$(R$^2$)$_p$Si—R$^3$—SH with a sulfenamide group-containing compound of the formula (6): (R$^5$)(R$^6$)N—S—R$^4$—B, use of a solvent is arbitrary. Examples of the solvent, if used, include hydrocarbons such as pentane, hexane, heptane, octane, benzene, toluene and xylene, alcohols such as methanol and ethanol, ethers such as dibutyl ether, tetrahydrofuran and dioxane, ketones such as methyl ethyl ketone and methyl isobutyl ketone, esters such as ethyl acetate, and amides such as dimethylformamide. The reaction temperature is generally in the range of about 0° C. to 150° C., preferably about 50° C. to 100° C. The reaction time may continue until either the compound of formula (5) or (6) is consumed, and generally ranges from about 30 minutes to about 20 hours. The way of reaction is arbitrary and, for example, involves charging the compounds of formulae (5) and (6) and optionally, solvent, and heating the charge. The molar ratio of the compound (5) to the compound (6) during reaction may be 1:0.9–1.1.

When the organosilicon compound is prepared by reacting a sulfenamide group-containing organosilicon compound of the formula (7): (R$^1$O)$_{(3-p)}$(R$^2$)$_p$Si—R$^3$—S—N(R$^5$)(R$^6$) with a mercapto group-containing compound of the formula (8): HS—R$^4$—Z, use of a solvent is arbitrary. Examples of the solvent, if used, include hydrocarbons such as pentane, hexane, heptane, octane, benzene, toluene and xylene, alcohols such as methanol and ethanol, ethers such as dibutyl ether, tetrahydrofuran and dioxane, ketones such as methyl ethyl ketone and methyl isobutyl ketone, esters such as ethyl acetate, and amides such as dimethylformamide. The reaction temperature is generally in the range of about 0° C. to 150° C., preferably about 50° C. to 100° C. The reaction time may continue until either the compound of formula (7) or (8) is consumed, and generally ranges from about 30 minutes to about 20 hours. The way of reaction is arbitrary and, for example, involves charging the compounds of formulae (7) and (8) and optionally, solvent, and heating the charge. The molar ratio of the compound (7) to the compound (8) during reaction may be 1:0.9–1.1.

It is noted that the organosilicon compound of the invention can be prepared from a compound of the following general formula (9):

(R$_1$O)$_{(3-p)}$(R$^2$)$_p$Si—R$^3$—S$_m$—Na          (9)

wherein $R^1$, $R^2$, $R^3$ and m are as defined above and a compound of the following general formula (10):

$$X\text{—}R^4\text{—}Y \quad (10)$$

wherein $R^4$, X and Y are as defined above; or from a compound of the following general formula (11):

$$(R_1O)_{(3-p)}(R^2)_p Si\text{—}R^3\text{—}X \quad (11)$$

wherein $R^1$, $R^2$, $R^3$ and X are as defined above and a compound of the following general formula (12):

$$Na\text{—}S_m R^4\text{—}Z \quad (12)$$

wherein Z is hydrogen or —$S_m$—Na, $R^4$ and m are as defined above. Although the inventive compounds of high purity can be synthesized, these synthesis processes are less preferable because the starting reactants are expensive.

The inventive organosilicon compounds are advantageously used as interfacial binders between inorganic materials such as silica, aluminum hydroxide and talc and organic materials such as thermosetting resins, thermoplastic resins and rubber, adhesion modifiers, surface treating agents and other agents applicable to such materials. In these applications, compositions obtained by adding the inventive organosilicon compounds to resins or rubber and mixing with inorganic materials are fully resistant to abrasion.

It is presumed that the preparation processes according to the invention entail formation as impurities of compounds having the following general formula (13):

$$(R^1O)_{(3-p)}(R^2)_p Si\text{—}R^3\text{—}S_m\text{—}R^3\text{—}Si(R^2)_p(OR^1)_{(3-p)} \quad (13)$$

wherein $R^1$, $R^2$, $R^3$ and m are as defined above, and compounds having the following general formula (14):

$$D\text{—}(R^4\text{—}S_m\text{—}R^4\text{—}E)_s\text{—} \quad (14)$$

wherein D is hydrogen or a valence bond to E, E is hydrogen or —$S_m$—, s is an integer of at least 1, $R^4$ and m are as defined above. However, the inclusion of these impurities in the reaction product does not impede the use of the inventive compound, such as addition to rubber or organic resins or surface treatment of inorganic fillers.

EXAMPLE

Examples of the invention are given below by way of illustration and not by way of limitation.

Example 1

A 1-liter separable flask equipped with a nitrogen gas inlet, thermometer, Dimroth condenser and dropping funnel was charged with 250 g of ethanol, 78 g (1.0 mol) of anhydrous sodium sulfide, and 32 g (1.0 mol) of sulfur. A mixture of 240.5 g (1.0 mol) of 3-chloropropyltriethoxysilane and 120.5 g (1.0 mol) of n-hexyl chloride was added dropwise to the flask at 75° C. This dropwise addition took 50 minutes. At the end of dropwise addition, the reaction solution was ripened for 8 hours, and then filtered. The filtrate was concentrated in vacuum in a rotary evaporator, leaving 271.1 g of a brown clear liquid. It had a viscosity of 5.6 mm²/s at 25° C. and an index of refraction of 1.4673 at 25° C. On analysis by infrared absorption spectroscopy and proton nuclear magnetic resonance (NMR) spectroscopy, it was confirmed to be a sulfide group-containing alkoxysilane having the average compositional formula below.

$$(CH_3CH_2O)_3Si(CH_2)_3\text{—}S_2\text{—}(CH_2)_5CH_3$$

Example 2

Reaction was carried out as in Example 1 except that 176.5 g (1.0 mol) of n-decyl chloride was used instead of n-hexyl chloride. There was obtained 322.7 g of a brown clear liquid. On analysis by IR spectroscopy and proton NMR spectroscopy, it was confirmed to be a sulfide group-containing alkoxysilane having the average compositional formula below.

$$(CH_3CH_2O)_3Si(CH_2)_3\text{—}S_2\text{—}(CH_2)_9CH_3$$

Example 3

Reaction was carried out as in Example 1 except that 198.5 g (1.0 mol) of 3-chloropropyltrimethoxysilane was used instead of 3-chloropropyltriethoxysilane and methanol used instead of ethanol. There was obtained 230.5 g of a brown clear liquid. On analysis by IR spectroscopy and proton NMR spectroscopy, it was confirmed to be a sulfide group-containing alkoxysilane having the average compositional formula below.

$$(CH_3O)_3Si(CH_2)_3\text{—}S_2\text{—}(CH_2)_5CH_3$$

Example 4

Reaction was carried out as in Example 1 except that the amount of sulfur used was changed to 64 g (2.0 mol). There was obtained 272.1 g of a brown clear liquid. On analysis by IR spectroscopy and proton NMR spectroscopy, it was confirmed to be a sulfide group-containing alkoxysilane having the average compositional formula below.

$$(CH_3CH_2O)_3Si(CH_2)_3\text{—}S_3\text{—}(CH_2)_5CH_3$$

Example 5

Reaction was carried out as in Example 1 except that 174 g (1.0 mol) of anhydrous sodium tetrasulfide was used instead of anhydrous sodium sulfide and sulfur. There was obtained 257.8 g of a brown clear liquid. On analysis by IR spectroscopy and proton NMR spectroscopy, it was confirmed to be a sulfide group-containing alkoxysilane having the average compositional formula below.

$$(CH_3O)_3Si(CH_2)_3\text{—}S_4\text{—}(CH_2)_5CH_3$$

Example 6

Reaction was carried out as in Example 1 except that 285 g (1.0 mol) of 6-bromohexyltrimethoxysilane was used instead of 3-chloropropyltriethoxysilane. There was obtained 283.1 g of a brown clear liquid. On analysis by IR spectroscopy and proton NMR spectroscopy, it was confirmed to be a sulfide group-containing alkoxysilane having the average compositional formula below.

$$(CH_3O)_3Si(CH_2)_6\text{—}S_2\text{—}(CH_2)_5CH_3$$

Example 7

Reaction was carried out as in Example 1 except that 77.5 g (0.5 mol) of dichlorohexane was used instead of n-hexyl chloride. There was obtained 292.4 g of a brown clear liquid. On analysis by IR spectroscopy and proton NMR spectroscopy, it was confirmed to be a sulfide group-containing alkoxysilane having the average compositional formula below.

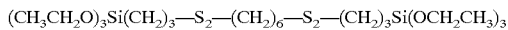

Example 8

A 1-liter separable flask equipped with a nitrogen gas inlet, thermometer, Dimroth condenser and dropping funnel was charged with 238.0 g (1.0 mol) of 3-mercaptopropyltriethoxysilane and 203.0 g (1.0 mol) of a sulfenamide of the formula: $(CH_3)_3C-NH-S(CH_2)_5CH_3$. The contents were ripened at 95° C. for 5 hours. The reaction solution was concentrated in vacuum in a rotary evaporator for removing by-product t-butylamine, leaving 323.6 g of a brown clear liquid. On analysis by IR spectroscopy and proton NMR spectroscopy, it was confirmed to be a sulfide group-containing alkoxysilane having the average compositional formula below.

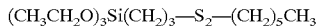

Example 9

A 1-liter separable flask equipped with a nitrogen gas inlet, thermometer, Dimroth condenser and dropping funnel was charged with 118.0 g (1.0 mol) of n-hexylmercaptan and 323.0 g (1.0 mol) of a sulfenamide of the formula shown below.

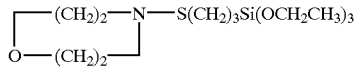

The contents were ripened at 95° C. for 10 hours. The reaction solution was concentrated in vacuum in a rotary evaporator for removing by-product morpholine, leaving 327.9 g of a brown clear liquid. On analysis by IR spectroscopy and proton NMR spectroscopy, it was confirmed to be a sulfide group-containing alkoxysilane having the average compositional formula below.

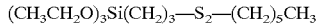

Example 10

Reaction was carried out as in Example 9 except that 74.0 g (1.0 mol) of allylmercaptan was used instead of n-hexylmercaptan, 200 g of toluene was used as the solvent, and the reaction temperature was 50° C. There was obtained 275.9 g of a brown clear liquid. On analysis by IR spectroscopy and proton NMR spectroscopy, it was confirmed to be a sulfide group-containing alkoxysilane having the average compositional formula below.

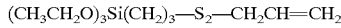

There have been described organosilicon compounds which are useful as a compounding additive to inorganic-organic composite materials and a surface treating agent for fillers, The processes of the invention ensure effective preparation of these organosilicon compounds.

Japanese Patent Application No. 2001-107982 is incorporated herein by reference.

Reasonable modifications and variations are possible from the foregoing disclosure without departing from either the spirit or scope of the present invention as defined by the claims.

What is claimed is:

1. A process for preparing an organosilicon compound having the following formula (1):

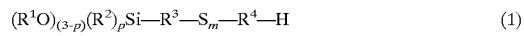

wherein $R_1$ and $R^2$ each are a monovalent hydrocarbon group having 1 to 4 carbon atoms, $R^3$ and $R^4$ each are a divalent hydrocarbon group having 1 to 10 carbon atoms, m is 2 to 10, and p is equal to 0, 1 or 2, comprising the step of reacting a haloalkyl group-containing organosilicon compound of the following formula (2):

wherein $R^1$, $R^2$ and $R^3$ and p are defined above and X is halogen, and a halogen-containing compound of the following formula (3):

wherein $R^4$ and X are as defined above with an anhydrous sodium sulfide or polysulfide having the following formula (4):

wherein q is 1 to 4, and optionally, sulfur.

2. A process for preparing an organosilicon compound having the following formula (1):

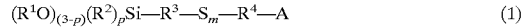

wherein $R^1$ and $R^2$ each are a monovalent hydrocarbon group having 1 to 4 carbon atoms, $R^3$ and $R^4$ each are a divalent hydrocarbon group having 1 to 10 carbon atoms, A is hydrogen or the moiety: $-S_m-R^3-Si(OR^1)_{(3-p)}(R^2)_p$, m is 2 to 10, and p is equal to 0, 1 or 2, comprising the step of reacting a mercaptoalkyl group-containing organosilicon compound of the following formula (5):

wherein $R^1$, $R^2$, $R^3$ and p are as defined above, with a sulfenamide group-containing compound of the following formula (6):

wherein $R^4$ is a divalent hydrocarbon group having 1 to 10 carbon atoms, $R^5$ and $R^6$ each are independently selected from the group consisting of hydrogen, methyl, ethyl, n-propyl, i-propyl, $-C(CH_3)_3$, vinyl, allyl, and phenyl groups, with the proviso that $R^5$ and $R^6$ are not hydrogen at the same time, or $R^5$ and $R^6$, taken together, form $-(CH_2)_2-O-(CH_2)_2-$, and B is hydrogen or the moiety: $-S-N(R^5)(R^6)$.

3. A process for preparing an organosilicon compound having the formula (1):

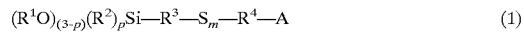

wherein $R^1$ and $R^2$ each are a monovalent hydrocarbon group having 1 to 4 carbon atoms, $R^3$ and $R^4$ each are a divalent hydrocarbon group having 1 to 10 carbon atoms, A is hydrogen or the moiety: $-S_m-R^3-Si$ $(OR^1)_{(3-p)}(R^2)_p$, m is 2 to 10, and p is equal to 0, 1 or 2, comprising the step of reacting a sulfenamide group-containing organosilicon compound of the following formula (7):

$$(R^1O)_{(3-p)}(R^2)_pSi—R^3—S—N(R^5)(R^6) \quad (7)$$

wherein $R^1$, $R^2$, $R^3$ and p are as defined above, $R^5$ and $R^6$ each are independently hydrogen or a monovalent hydrocarbon group having 1 to 6 carbon atoms, with the proviso that $R^5$ and $R^6$ are not hydrogen at the same time, or $R^5$ and $R^6$, taken together, form a divalent hydrocarbon group having 4 to 10 carbon atoms which may contain a nitrogen, oxygen or sulfur atom, with a mercapto group-containing compound of the following formula (8):

$$HS—R^4—Z \quad (8)$$

wherein $R^4$ is as defined above and Z is hydrogen or SH.

4. The process of claim 1, wherein:
   $R^1$ and $R^2$ are each selected from the group consisting of methyl, ethyl, n-propyl, i-propyl, n-butyl, i-butyl, t-butyl, allyl and methallyl;
   $R^3$ and $R^4$ are each independently selected from the group consisting of methylene, ethylene, propylene, n-butylene, i-butylene, hexylene, decylene, phenylene, and methylphenylethylene.

5. The process of claim 2, wherein:
   $R^1$ and $R^2$ are each selected from the group consisting of methyl, ethyl, n-propyl, i-propyl, n-butyl, i-butyl, t-butyl, allyl and methallyl; and
   $R^3$ and $R^4$ are each independently selected from the group consisting of methylene, ethylene, propylene, n-butylene, i-butylene, hexylene, decylene, phenylene, and methylphenylethylene.

6. The process of claim 3, wherein:
   $R^1$ and $R^2$ are each selected from the group consisting of methyl, ethyl, n-propyl, i-propyl, n-butyl, i-butyl, t-butyl, allyl and methallyl; and
   $R^3$ and $R^4$ are each independently selected from the group consisting of methylene, ethylene, propylene, n-butylene, i-butylene, hexylene, decylene, phenylene, and methylphenylethylene.

7. The process of claim 1, wherein the compound of formula (2) is selected from the group consisting of:
   $(CH_3O)_3Si—(CH_2)_3—Cl$,
   $(CH_3CH_2O)_3Si—(CH_2)_3—Cl$,
   $(CH_3O)_3Si—(CH_2)_4Cl$,
   $(CH_3O)_3Si—(CH_2)_6—Br$,
   $(CH_3O)_3Si—(CH_2)_{10}—Br$,
   $(CH_3O)_3Si—CH_2CH(CH_3)CH_2—Cl$, and
   $(CH_3CH_2O)_3Si—CH_2CH(CH_3)CH_2—Cl$.

8. The process of claim 1, wherein the compound of formula (3) is selected from the group consisting of:
   $Cl—CH_2CH_2CH_2CH_3$,
   $Cl—(CH_2)_5CH_3$,
   $Cl—(CH_2)_9CH_3$,
   $Cl—CH_2CH=CH_2$,
   $Cl—(CH_2)_6—Cl$,
   $Br—(CH_2)_5CH_3$, and
   $Cl—CH_2C(CH_3)=CH_2$.

9. The process of claim 1, wherein the compound of formula (4) is selected from the group consisting of:
   $Na_2S$, $Na_2S_2$, $Na_2S_3$ and $Na_2S_4$.

10. The process of claim 2, wherein the compound of formula (5) is selected from the group consisting of:
    $(CH_3O)_3Si—(CH_2)_3—SH$,
    $(CH_3CH_2O)_3Si—(CH_2)_3—SH$,
    $(CH_3O)_3Si—(CH_2)_4—SH$,
    $(CH_3O)_3Si—(CH_2)_6—SH$,
    $(CH_3O)_3Si—(CH_2)_{10}—SH$,
    $(CH_3O)_3Si—CH_2CH(CH_3)CH_2—SH$, and
    $(CH_3CH_2O)_3Si—CH_2CH(CH_3)CH_2—SH$.

11. The process of claim 2, wherein the compound of formula (6) is selected from the group consisting of:
    $(CH_3)_3C—NH—S—CH_2CH_2CH_2CH_3$,
    $(CH_3)_3C—NH—S—(CH_2)_5CH_3$,
    $(CH_3)_3C—NH—S—(CH_2)_9CH_3$,
    $(CH_3)_3C—NH—S—CH_2CH=CH_2$,
    $(CH_3)_3C—NH—S—(CH_2)_6—S—NHC(CH_3)_3$, and $$\begin{array}{c} \overline{\phantom{xx}}(CH_2)_2—N—S—(CH_2)_5CH_3. \\ O—(CH_2)_2\underline{\phantom{xx}} \end{array}$$

12. The method of claim 3, wherein the compound of formula (7) is selected from the group consisting of:
    $(CH_3O)_3Si—(CH_2)_3—S—NH—C(CH_3)_3$,
    $(CH_3CH_2O)_3Si—(CH_2)_3—S—NH—C(CH_3)_3$,
    $(CH_3O)_3Si—(CH_2)_4—S—NH—C(CH_3)_3$,
    $(CH_3O)_3Si—(CH_2)_6—S—NH—C(CH_3)_3$,
    $(CH_3O)_3Si—(CH_2)_{10}—S—NH—C(CH_3)_3$,
    $(CH_3O)_3Si—CH_2CH(CH_3)CH_2—S—NH—C(CH_3)_3$,
    $(CH_3CH_2O)_3Si—CH_2CH(CH_3)CH_2—S—NH—C(CH_3)_3$.

$$(CH_3O)_3Si—(CH_2)_3—S—N\begin{array}{c}\overline{\phantom{x}}(CH_2)_2—O\\(CH_2)_2\underline{\phantom{x}}\end{array}, \text{ and}$$

$$(CH_3CH_2O)_3Si—(CH_2)_3—S—N\begin{array}{c}\overline{\phantom{x}}(CH_2)_2—O\\(CH_2)_2\underline{\phantom{x}}\end{array}.$$

13. The process of claim 3, wherein the compound of formula (8) is selected from the group consisting of:
    $HS—CH_2CH_2CH_2CH_3$,
    $HS—(CH_2)_5CH_3$,
    $HS—(CH_2)_9CH_3$,
    $HS—CH_2CH=CH_2$,
    $HS—(CH_2)_6—SH$, and
    $HS—CH_2C(CH_3)=CH_2$.

* * * * *